United States Patent
Hung et al.

[11] 3,979,511
[45] Sept. 7, 1976

[54] INHIBITORS OF REVERSE TRANSCRIPTASE ENZYMES

[75] Inventors: Paul P. Hung; Nathan L. Shipkowitz, both of Waukegan; Anne Mary Von Esch, North Chicago, all of Ill.

[73] Assignee: Abbott Laboratories, North Chicago, Ill.

[22] Filed: May 23, 1974

[21] Appl. No.: 472,564

[52] U.S. Cl.................................. 424/181; 424/180
[51] Int. Cl.²........................................... A61K 31/71
[58] Field of Search............................ 424/180, 181

[56] References Cited
UNITED STATES PATENTS 3,681,326 8/1972 Von Esch....................... 260/210 E Primary Examiner—Jerome D. Goldberg
Attorney, Agent, or Firm—Robert L. Niblack; Vincent A. Mallare

[57] ABSTRACT

A method of inhibiting the activity of reverse transcriptase in Rous sarcoma viruses and other viruses containing reverse transcriptase. The method comprises subjecting the reverse transcriptase to an enzyme inhibiting effective dosage of a compound of the formula:

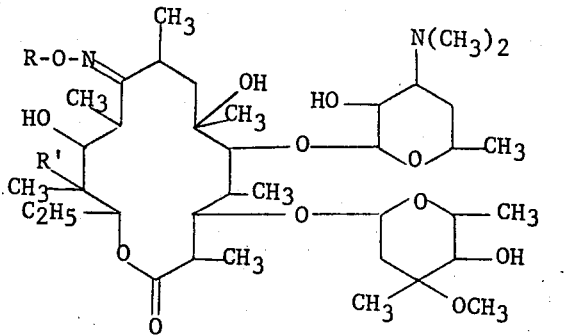

wherein R' is hydrogen or hydroxyl and R is $C_1$–$C_8$ alkyl, cyclohexyl, phenyl, benzyl, and substituted benzyl.

6 Claims, No Drawings

INHIBITORS OF REVERSE TRANSCRIPTASE ENZYMES

BACKGROUND OF THE INVENTION

This invention is related to a method of inhibiting the activity of reverse transcriptase in viruses such as Rous sarcoma in warm-blooded animals such as chickens.

Reverse transcriptase (RNA dependent DNA polymerase) occurs uniquely in the virions of all members of a group of viruses which cause cancer in animals and probably in man. The viruses in this group include all of the transforming (sarcoma) C type viruses, the non-transforming (leukemia) C type viruses, and the mammary tumor (B type) virus. Also included are visna, maedi, and progressive pneumonia viruses which cause slow degenerative diseases and the foamy (syncytium forming) viruses. Visna and progressive pneumonia viruses can cause transformation of mouse cells in vitro. Human breast cancers contain an RNA related to that of mouse mammary tumor virus. The RNA is encapsulated with reverse transcriptase in a particle possessing the density characteristics of RNA tumor viruses (Axel, R., S. C. Gulati, and S. Spiegelman, Proc. Nat. Acad. Sci. U.S.G. 69, 3133 (1972). Similarly, complexes of RNA and reverse transcriptase have been identified in the white blood cells of leukemic patients (Baxt. W., R. Hehlmann, S. Spiegelman, Nature, 240, 72 (1972). Moreover, nononcogenic RNA viruses have been found to lack reverse transcriptase. The following viruses belong to this category: Reo, Polio, Influenza, Vesticular stomatitis, New Castle disease (Nature, 227, 1029 (1970). Evidence implicating reverse transcriptase in cell transformation is provided by the following observations:

1. A variant of Rous sarcoma virus RSVα (0) which failed to transform chick fibroblasts, lacked the enzyme (Hanafusa, H., and Hanafusa, T. Virology 43, 313 (1971);

2. A temperature sensitive mutant of Rous sarcoma virus which was unable either to transform or replicate at 41°C. but could do both functions at 35°C. contained reverse transcriptase, functional at 35°C. but not at 41°C. (Linial, M., and W. S. Mason, Virology 53, 258 (1973); and 3. The reverse transcriptase and transforming activities of Rous sarcoma virus could be destroyed by a chemical. However, the chemically inactivated virus recovered its transforming activity when coinfected with a nontransforming leukosis virus which possessed active reverse transcriptase (P. P. Hung, Virology 53, 463 (1973).

DISCLOSURE OF THE INVENTION

This invention relates to a method of inhibiting the activity of enzymes. More particularly, this invention provides a method for inhibiting the activity of reverse transcriptase enzyme in Rous sarcoma viruses (RSV). The method comprises subjecting the reverse transcriptase enzyme in Rous sarcoma virus to an enzyme inhibiting effective dosage of a compound having the general structure:

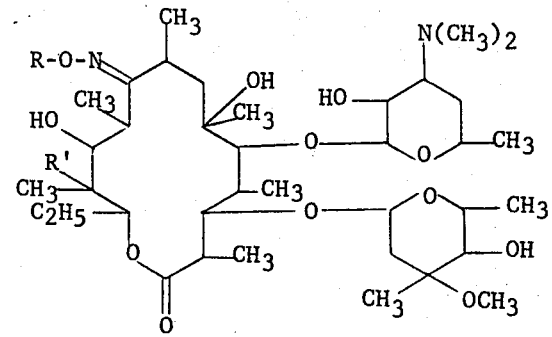

wherein R' is hydrogen or hydroxyl and R is $C_1$–$C_8$ alkyl, cyclohexyl, phenyl, benzyl, or substituted benzyl.

The compounds of the present invention have been found to be an effective inhibitor of reverse transcriptase in Rous sarcoma virus (RSV). The compounds useful for inhibiting the activity of the reverse transcriptase are oximinyl derivatives of erythromycin. The preferred oximinyl derivatives of erythromycin are 9-0-methyloximinyl erythromycin A, 9-0-ethyloximinyl erythromycin A, and 9-0-(3,4-dichlorobenzyloximinyl) erythromycin B. These compounds can be prepared by the process which is fully disclosed in U.S. Pat. No. 3,681,326, issued August 1, 1972.

The present method thus provides a means of combating a virus infection or disease in a susceptible host for Rous sarcoma virus. The method provides a means of inhibiting the activity of reverse transcriptase in such virus as Rous sarcoma virus.

The following examples will further illustrate the advantages and use of the present invention.

EXAMPLE I

Inhibition of reverse transcriptase activity in RSV particles by 9-0-methyloximinyl erythromycin A is demonstrated below in the Graph - "Inhibition of Reverse Transcriptase Activity". Inhibition was directly related to drug concentration. Fifty percent inhibition was observed at approximately 350 μg/ml. Reverse transcriptase activities were measured from the incorporation of $^3$H-thymidine triphosphate into trichloroacetic acid insoluble counts according to a published method (Nature, 227, 563 (1970). The drug was dissolved in dimethylsulfoxide at a concentration of 10 mg./ml.

INHIBITION OF REVERSE TRANSCRIPTASE ACTIVITY

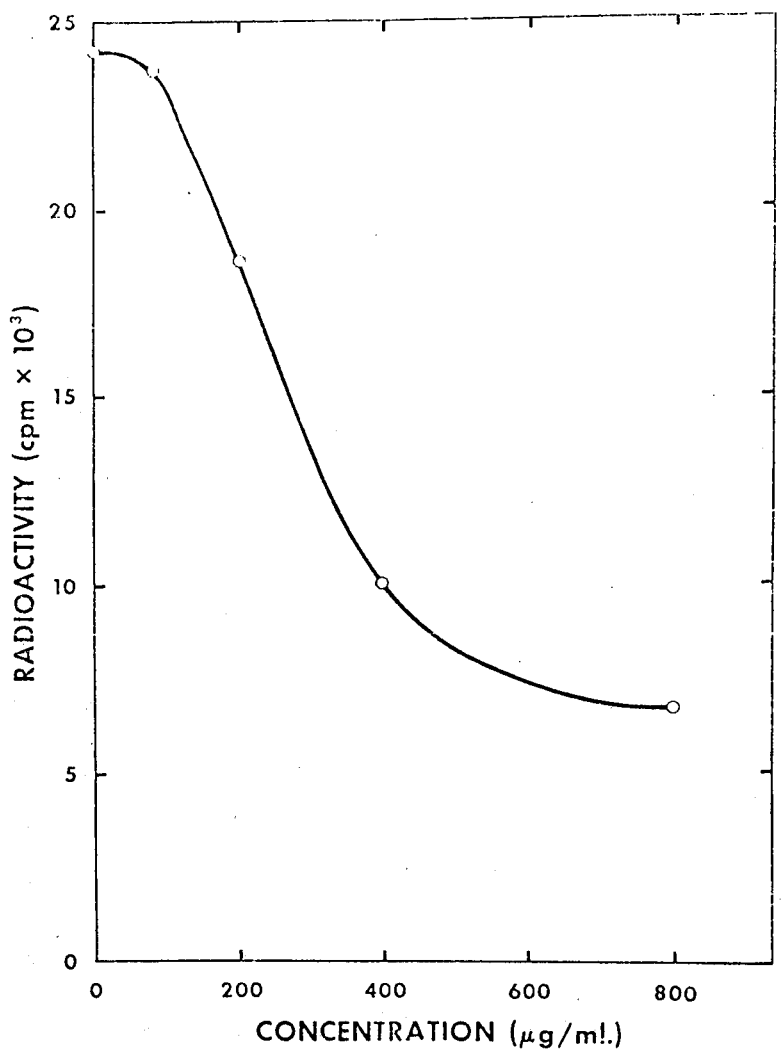

EXAMPLE II

Other oxime derivatives of erythromycin also possess inhibitory activities on reverse transcriptase of Rous sarcoma virus. Degrees of the inhibition are listed below in Table 1.

TABLE 1

Inhibition of Reverse Transcriptase by Oxime Derivatives of Erythromycin

| Compounds (400 μg/ml.) | Percent Inhibition |
| --- | --- |
| None | 0 |
| 9-O-methyloximinyl erythromycin A | 57 |
| 9-O-ethyloximinyl erythromycin A | 52 |
| 9-O-propyloximinyl erythromycin A | 47 |
| 9-O-(3,4-dichlorobenzyloximinyl) erythromycin B | 69 |

EXAMPLE III

In tissue culture, the effect of 9-0-methyloximinyl erythromycin A on the blocking of transformation of chick embryonic fibroblasts by Rous sarcoma virus is shown in Table 2. The compound inhibited at least 50% of focus formation at drug levels of 5-10 μg/ml. The assay was carried out according to a published method (J. Gen. Virol. I, 85 (1970).

Table 2

Inhibition of Focus-Forming Units (FFU) by 9-O-Methyloximinyl Erythromycin A

| Drug Concentration (μg/ml) | FFU/Plate (duplicates) | Inhibition (%) |
| --- | --- | --- |
| 0 | 168, 179 | — |
| 1 | 111, 99 | 39 |
| 5 | 74, 89 | 53 |
| 10 | 6, 12 | 95 |

EXAMPLE IV

To test the effectiveness of the present compounds, 12-day-old Cofal negative chicks were used. The chicks were purchased from SPAFA as 8-day-old embryonated eggs for the tests and comparison of the effectiveness of the inhibitors of the present invention. The chicks were divided into four groups of 25 birds per group:

Group 1 - Drug I control (9-0-methyloximinyl erythromycin A;
Group 2 - Drug I + Rous sarcoma virus (RSV);
Group 3 - Rous sarcoma virus (infection control);
Group 4 - Normal control (sham media)

The medication with the virus and drug combinations was started by gavage two days before the chicks were infected with the virus. The chickens treated with Drug I, 9-0-methyloximinyl erythromycin A, received 200 mg./kg. every other day for the entire 35 days of the experiment. Each week the chickens were weighed and the drug level was adjusted to accommodate the new weight.

On the third day the chickens in Groups 2 and 3 were infected intra-abdominally with Rous sarcoma virus (RSV). The inoculum received by each bird was 0.2 ml. and contained approximately 100,000 viral particles. Group 4 received a sham inoculation of 0.2 ml. of sterile tissue culture media.

The chickens were observed daily for the 35 days that the experiment was allowed to continue.

On the last day, the 35th day, all surviving chickens were sacrificed, weighed and autopsied.

In the observation of the chickens it was observed that the birds that died from tumors produced by Rous sarcoma virus were found to have razor thin keels, pectoral muscles that were dry and taut and viscera bulged against the abdominal wall. When the abdomen was opened, yellow viscous fluid drained from the cavity. Numerous tumors were found throughout the abdominal cavity, often extending into the thorax or attached to the liver.

In the two groups of birds that were infected with Rous sarcoma virus, all survivors, including those that had received Drug I, had tumors in evidence when they were sacrificed and autopsied.

The results of the experiment are provided in Table 3 which provides the following results: "Statistical Evaluation of Mortality of the Chickens".

I claim:
1. A method for inhibiting the activity of reverse transcriptase in Rous sarcoma viruses in an animal which comprises administering to an animal being infected with said virus an effective amount for inhibiting said enzyme of a compound of the formula

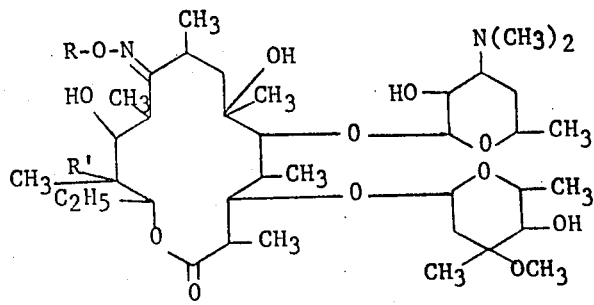

wherein $R^1$ is hydrogen or hydroxyl and R is $C_1$-$C_8$ alkyl, cyclohexyl, phenyl, benzyl and 3,4 dichlorobenzyl.

2. The method of claim 1 wherein said compound is administered to said animal in dosages of from 50 to 100 mg./kg. of body weight daily.

3. The method of claim 1 wherein the compound

TABLE 3

| Group | Statistical Evaluation of Mortality Chi-Square Test for Independence in a Two-Way Classification Periods After Infection* | | | | | | | | |
|---|---|---|---|---|---|---|---|---|---|
| | 0–3 | 4 | | | 5 | | | 6 | |
| | | Dead | Alive | Probability | Dead | Alive | Probability | Dead | Alive | Probability |
| Virus | ** | 15 | 10 | — | 22 | 3 | — | 23 | 2 | — |
| Virus + Drug I | ** | 7 | 18 | .02*** | 12 | 13 | .006*** | 17 | 8 | .036*** |
| Drug I | — | 0 | 25 | — | 0 | 25 | — | 0 | 25 | — |

*Period = 6 days
**There were not enough dead chickens in periods 0–3 to carry out a statistical evaluation
***Fisher's exact probability for proportions In the practice of this invention, the compounds of the present invention, 9-0-methyloximinyl erythromycin A, 9-0-ethyloximinyl erythromycin A and 9-0-(3,4-dichlorobenzyloximinyl) erythromycin B may be administered orally or parenterally in dosages of from 50 to 100 mg./kg. of body weight per day. It is well understood by those skilled in the art that dosage regimens are often complex and may vary from patient to patient. Generally speaking, however, the drug is administered in single dosages for 10 to 30 days. Maintenance dosages may be administered weekly or monthly depending on the progress of the patient. The drugs of the present invention may be administered in tablet form or by injection intravenously depending upon what is needed and the convenience in the administration of the drug.

administered to said animal is 9-0-methyloximinyl erythromycin A.

4. The method of claim 1 wherein the compound administered to said animal is 9-0-ethyloximinyl erythromycin A.

5. A method of treating viral infections caused by Rous sarcoma virus in an animal so infected comprising administering to said animal an effective amount for combating said virus infection with an oximinyl derivative of erythromycin selected from the group consisting of 9-0-methyloximinyl erythromycin A, 9-0-ethyloximinyl erythromycin A and 9-0-(3,4-dichlorobenzyloximinyl)erythromycin B.

6. A method according to claim 5, wherein said compound is administered to said animal in parenteral dosages of from 50 to 100 mg./kg. of body weight daily.

* * * * *